(12) United States Patent
Heidenreich et al.

(10) Patent No.: US 7,846,907 B2
(45) Date of Patent: Dec. 7, 2010

(54) DOUBLE-STRANDED RNA (DSRNA) AND METHOD OF USE FOR INHIBITING EXPRESSION OF A FUSION GENE

(75) Inventors: Olaf Heidenreich, Tübgingen (DE); Hans-Peter Vornlocher, Bayreuth (DE); Roland Kreutzer, Weidenberg (DE); Stefan Limmer, Neudrossenfeld (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/656,349

(22) Filed: Jan. 22, 2007

(65) Prior Publication Data

US 2007/0185050 A1    Aug. 9, 2007

Related U.S. Application Data

(62) Division of application No. 10/349,320, filed on Jan. 22, 2003, now Pat. No. 7,196,184.

(30) Foreign Application Priority Data

Jan. 22, 2002    (DE) ................ 102 02 419

(51) Int. Cl.
*A61K 48/00* (2006.01)

(52) U.S. Cl. .................. 514/44; 536/24.5; 536/24.31; 536/24.3

(58) Field of Classification Search .............. None
See application file for complete search history.

(56) References Cited

U.S. PATENT DOCUMENTS

| | | | |
|---|---|---|---|
| 5,912,332 A | 6/1999 | Agrawal et al. | |
| 6,423,489 B1 | 7/2002 | Anderson et al. | 435/6 |
| 6,486,299 B1 | 11/2002 | Shimkets | 530/350 |
| 6,506,559 B1 | 1/2003 | Fire et al. | 435/6 |
| 2002/0086356 A1 | 7/2002 | Tuschl et al. | 435/69.1 |
| 2002/0114784 A1 | 8/2002 | Li et al. | 424/93.2 |
| 2002/0123034 A1 | 9/2002 | Canaani et al. | 435/4 |
| 2002/0132346 A1 | 9/2002 | Cibelli | 435/455 |
| 2002/0162126 A1 | 10/2002 | Beach et al. | 800/8 |
| 2002/0173478 A1 | 11/2002 | Gewirtz | 514/44 |
| 2003/0027783 A1 | 2/2003 | Zernicka-Goetz et al. | 514/44 |
| 2003/0108923 A1 | 6/2003 | Tuschl et al. | 435/6 |
| 2003/0125281 A1 | 7/2003 | Lewis et al. | 514/44 |
| 2003/0143732 A1 | 7/2003 | Fosnaugh et al. | 435/325 |
| 2003/0148341 A1 | 8/2003 | Sin et al. | 435/6 |
| 2003/0157030 A1 | 8/2003 | Davis et al. | 424/46 |
| 2003/0176671 A1 | 9/2003 | Reed et al. | 536/23.1 |
| 2003/0180756 A1 | 9/2003 | Shi et al. | 435/6 |
| 2003/0190635 A1 | 10/2003 | McSwiggen | 435/6 |
| 2003/0198627 A1 | 10/2003 | Arts et al. | 424/93.21 |
| 2004/0203011 A1 | 10/2004 | Morris et al. | |

FOREIGN PATENT DOCUMENTS

| | | |
|---|---|---|
| DE | 199 03 713 | 1/1999 |
| DE | 19956568 A1 | 11/1999 |
| DE | 20023125 U1 | 1/2000 |
| DE | 10100588 A1 | 1/2001 |
| DE | 10163098 A1 | 12/2001 |
| DE | 10235620.3 | 1/2002 |
| DE | 10100586 C1 | 4/2002 |
| DE | 10230996 A1 | 7/2002 |
| DE | 10230997 A1 | 7/2002 |
| EP | 1214945 A2 | 1/2000 |
| WO | WO 99/32619 | 7/1999 |
| WO | WO 99/53050 | 10/1999 |
| WO | WO 99/61631 | 12/1999 |
| WO | WO 00/01846 | 1/2000 |
| WO | 00/44895 | 8/2000 |
| WO | WO 00/44914 | 8/2000 |
| WO | WO 00/63364 | 10/2000 |
| WO | WO 00/68374 | 11/2000 |
| WO | WO 01/18197 A1 | 3/2001 |
| WO | WO 01/29058 A1 | 4/2001 |
| WO | WO 01/36646 A1 | 5/2001 |
| WO | WO 01/42443 A1 | 6/2001 |
| WO | WO 01/48183 A2 | 7/2001 |
| WO | WO 01/68836 A2 | 9/2001 |
| WO | WO 01/70949 A1 | 9/2001 |
| WO | WO 01/75164 A2 | 10/2001 |
| WO | WO 02/44321 | 11/2001 |

(Continued)

OTHER PUBLICATIONS

Caplen NJ. RNAi as a Gene Therapy Approach. Expert Opinon. Biol. Thera. (2003) vol. 3(4) 575-586. Ashley Publications Ltd.*

Paroo et al. Challenges for RNAi in vivo. Trends in Biotechnology (2004), vol. 22(8) 390-394. Elsevier.*

Adams, A. RNA therapeutics enter clinical trials. Scientist (2005), vol. 19:Issue 1. Institute for Scientific Information.*

Hammond et al. Post-transcriptional gene silencing by double-stranded RNA Nature Reviews, 2001, vol. 2, 110-119. MacMillan Magazines Ltd.*

Matsushita et al. Ribozymes Cleave the AML1-MTG8 Fusion Transcript and Inhibit Proliferation of Leukemic Cells with t(8;21). Biochemical and Biophysical Research Communications, 1995, vol. 215, No. 2: 431-437.*

Novina et al. The RNAi Revolution. Nature 2004, vol. 430: 161-164. Nature Publishing Group.*

Holen, T. et al., (2002), "Positional effects of short interfering RNAs targeting the human coagulation trigger Tissue Factor", *Nucleic Acids Research*, 30(8):1757-1766.

Ambros, V., (2001), "Dicing Up RNAs", *Science*, 293:811-813.

Elbashir, S.M. et al., (2001), "Duplexes of 21-nucleotide RNAs mediate RNA interference in cultured mammalian cells", *Nature*, 411:494-498.

(Continued)

*Primary Examiner*—Kimberly Chong
(74) *Attorney, Agent, or Firm*—Fenwick & West LLP

(57) ABSTRACT

The present invention relates to the specific inhibition of expression of a fusion gene in mammals using a short double stranded RNA. The dsRNA is approximately 19-24 nucleotides in length, and has a nucleotide sequence which is complementary to at least a part of the target gene. The dsRNAs of the present invention are useful for treating diseases caused by chromosomal aberrations, particularly malignant diseases such as lymphoma and leukemia.

8 Claims, 2 Drawing Sheets

FOREIGN PATENT DOCUMENTS

| | | |
|---|---|---|
| WO | WO 01/92513 A1 | 12/2001 |
| WO | WO 02/16620 A2 | 2/2002 |
| WO | WO 02/26780 A2 | 4/2002 |
| WO | WO 02/44321 A2 * | 6/2002 |
| WO | WO 0244321 * | 6/2002 |
| WO | WO 02/055692 A2 | 7/2002 |
| WO | WO 02/055693 A2 | 7/2002 |
| WO | WO 02/061034 A2 | 8/2002 |
| WO | WO 02/068635 A2 | 9/2002 |
| WO | WO 02/068637 A2 | 9/2002 |
| WO | WO 03/006477 A1 | 1/2003 |
| WO | WO 03/012052 A2 | 2/2003 |
| WO | WO 03/012082 A2 | 2/2003 |
| WO | WO 03/016572 A1 | 2/2003 |
| WO | WO 03/033700 A1 | 4/2003 |
| WO | WO 03/035082 A1 | 5/2003 |
| WO | WO 03/035083 A1 | 5/2003 |
| WO | WO 03/035868 A1 | 5/2003 |
| WO | WO 03/035869 A1 | 5/2003 |
| WO | WO 03/035870 A1 | 5/2003 |
| WO | WO 03/035876 A1 | 5/2003 |
| WO | WO 03/070283 A2 | 8/2003 |
| WO | WO 03/070750 A2 | 8/2003 |
| WO | WO 03/070969 A2 | 8/2003 |
| WO | WO 03/070972 A2 | 8/2003 |
| WO | WO 03/074654 A2 | 9/2003 |
| WO | WO 03/080794 A2 | 10/2003 |
| WO | WO 03/080807 A2 | 10/2003 |

OTHER PUBLICATIONS

Gautschi, O. et al., (2001), "Activity of a Novel bcl-2/bcl-xL-Bispecific Antisense Oligonucleotide Against Tumors of Diverse Histologic Origins", *Journal of the National Cancer Institute*, 93(6):463-471.

Lipardi, C. et al., (2001), "RNAi as Random Degradative PCR: siRNA Primers Convert mRNA into dsRNAs that Are Degraded to Generate New siRNAs", *Cell*, 107:297-307.

Sharp, P.A., (2001), "RNA interference—2001", *Genes & Development*, 15:485-490.

Sijen, T. et al., (2001), "On the Role of RNA Amplification in dsRNA-Triggered Gene Silencing", *Cell*, 107:465-476.

Bass, B.L., (2000), "Double-Stranded RNA as a Template for Gene Silencing", *Cell*, 101:235-238.

Cobaleda, C. et al., (2000), "In vivo inhibition by a site-specific catalytic RNA subunit of Rnase P designed against the BCR-ABL oncogenic products: a novel approach for cancer treatment", *Blood*, 95(3):731-737.

Hammond, S.M. et al., (2000), "An RNA-directed nuclease mediates post-transcriptional gene silencing in *Drosophila* cells", *Nature*, 404:293-296.

Yang, D. et al., (2000), "Evidence that processed small dsRNAs may mediate sequence-specific mRNA degradation during RNAi in *Drosophila* embryos", *Current Biology*, 10:1191-1200.

Wianny, F. et al., (2000), "Specific interference with gene function by double-stranded RNA in early mouse development", *Nature Cell Biology*, 2:70-75.

Zamore, P.D. et al., (2000), "RNAi: Double-Stranded RNA Directs the ATP-Dependent Cleavage of mRNA at 21 to 23 Nucleotide Intervals", *Cell*, 101:25-33.

Fire, A., (1999), "RNA-triggered gene silencing", *TIG*, 15(9):358-363.

Tuschl, T. et al., (1999), "Targeted mRNA degradation by double-stranded RNA in vitro", *Genes & Development*, 13:3191-3197.

Wild, K. et al., (1999), "The 2 Å structure of helix 6 of the human signal recognition particle RNA", *Structure*, 7(11):1345-1352.

Montgomery, M.K. et al., (1998), "Double-stranded RNA as a mediator in sequence-specific genetic silencing and co-suppression", *TIG*, 14(7):255-258.

Lowy, D.R. et al., (1993), "Function and Regulation of RAS", *Annu. Rev. Biochem.*, 62:851-891.

Downward, J. et al., (1990), "Identification of a nucleotide exchange-promoting activity for $p21^{ras}$", *Proc. Natl. Acad. Sci. USA*, 87:5998-6002.

Gibbs, J.B. et al., (1988), "Purification of ras GTPase activating protein from bovine brain", *Proc. Natl. Acad. Sci. USA*, 85:5026-5030.

International Search Report of International Application No. PCT/EP02/00151.

Caplen, N.J., (2002), "A new approach to the inhibition of gene expression", *Trends in Biotechnology*, 20(2):49-51.

Caplen, N.J. et al., (2001), "Specific inhibition of gene expression by small double-stranded RNAs in invertebrate and vertebrate systems", *Proc. Natl. Acad. Sci. USA*, 98(17):9742-9747.

Doench, J.G. et al., (2003), "siRNAs can function as miRNAs", *Genes & Development*, 17:438-442.

Donzé, O. et al., (2002), "RNA interference in mammalian cells using siRNAs synthesized with T7 RNA Polymerase", *Nucleic Acids Research*, 30(10):e46(4pages).

Elbashir, S.M. et al., (2001), "RNA interference is mediated by 21- and 22-nucleotide RNAs", *Genes & Development*, 15:188-200.

Elbashir, S.M. et al., (2001), "Functional anatomy of siRNAs for mediating efficient RNAi in *Drosophila melanogaster* embryo lysate", *The EMBO Journal*, 20(23):6877-6888.

Fire, A. et al., (1998), "Potent and specific genetic interference by double-stranded RNA in *Caenorhabditis elegans*", *Nature*, 391:806-811.

Harborth, J. et al., (2001), "Identification of essential genes in cultured mammalian cells using small interfering RNAs", *Journal of Cell Science*, 114(24):4557-4565.

Lewis, D.L. et al., (2002), "Efficient delivery of siRNA for inhibition of gene expression in postnatal mice", *Nature Genetics*, 32:107-108.

Manche, L. et al., (1992), "Interactions between Double-Stranded RNA Regulators and the Protein Kinase DAI", *Molecular and Cellular Biology*, 12(11):5238-5248.

McCaffrey, A.P. et al., (2002), "RNA interference in adult mice", *Nature*, 418:38-39.

Ngô, H. et al., (1998), "Double-stranded RNA induces mRNA degradation in *Trypanosoma brucei*", *Proc. Natl. Acad. Sci.*, 95:14687-14692.

Paddison, P.J. et al., (2002), "Short hairpin RNAs (shRNAs) induce sequence-specific silencing in mammalian cells", *Genes & Development*, 16:948-958.

Randall, G. et al., (2003), "Clearance of replicating hepatitis C virus replicon RNAs in cell culture by small interfering RNAs", *PNAS*, 100(1):235-240.

Tijsterman, M. et al., (2002), "The Genetics of RNA Silencing", *Annu. Rev. Genet.*, 36:489-519.

Yu, J. et al., (2002), "RNA interference by expression of short-interfering RNAs and hairpin RNAs in mammalian cells", *PNAS*, 99(9):6047-6052.

Hammond et al., "Post-Transcriptional Gene Silencing by Double-stranded RNA" *Nature* 2:110-119, 2001.

Szyrach et al., "Cleavage of AML1/MTG8 by asymmetric hammerhead ribozymes" *Eur. J. Biochem.* 268:3550-3557, 2001.

Morelli et al., "The antisense bcl-2-IgH transcript is an optimal target for synthetic oligonucleotides" *Proc. Natl. Acad. Sci.* 94:8150-8155, 1997.

Krauter et al., "Depletion of AML1/MTG8 by Specific siRNAs Enables Modulation of Gene Expression by All Trans Retinoic Acid in t(8;21) Positive Kasumi-1 Cells" *Blood* vol. 100, No. 11, Abstract No. 2104, 2002.

Snyder et al., "Ribozyme-mediated inhibition of bcr-abl gene expression in a Philadelphia Chromosome-Positive cell line" *Blood* 82:600-605, 1993.

Matsushita et al. "Ribozymes cleave the aml1/mtg8 fusion transcript and inhibit proliferation of leukemic cells with t(8;21)" *Biochem. and Biophys. Res. Comm.* 215:431-437, 1995.

* cited by examiner

SEQUENCE LISTING

```
<160> NUMBER OF SEQ ID NOS: 20

<210> SEQ ID NO 1
<211> LENGTH: 23
<212> TYPE: RNA
<213> ORGANISM: Homo sapiens

<400> SEQUENCE: 1
cuucucagua cgauuucgag guu                                       23

<210> SEQ ID NO 2
<211> LENGTH: 21
<212> TYPE: RNA
<213> ORGANISM: Homo sapiens

<400> SEQUENCE: 2
ccucgaaauc guacugagaa g                                         21

<210> SEQ ID NO 3
<211> LENGTH: 23
<212> TYPE: RNA
<213> ORGANISM: Escherichia coli

<400> SEQUENCE: 3
ucaugcgaaa cgauccucau ccu                                       23
```

```
<210> SEQ ID NO 4
<211> LENGTH: 21
<212> TYPE: RNA
<213> ORGANISM: Escherichia coli

<400> SEQUENCE: 4
gaugaggauc guuucgcaug a                                              21

<210> SEQ ID NO 5
<211> LENGTH: 23
<212> TYPE: RNA
<213> ORGANISM: Hepatitis C virus

<400> SEQUENCE: 5
ggaccuuuca cagcuagccg uga                                            23

<210> SEQ ID NO 6
<211> LENGTH: 21
<212> TYPE: RNA
<213> ORGANISM: Hepatitis C virus

<400> SEQUENCE: 6
acggcuagcu gugaaagguc c                                              21

<210> SEQ ID NO 7
<211> LENGTH: 315
<212> TYPE: RNA
<213> ORGANISM: Homo sapiens

<400> SEQUENCE: 7
gggcgaauug gagcuccacc gcgguggcgg ccgcucuaga acuaguggau cccccaacgu     60
ugucggugua aaugaacugg uucuuggagc uccuugagua guuggggag guggcauugu     120 uggaggaguc agccuagauu gcgucuucac auccacaggu gagucuggca uuguggagug   180
cuucucagua cgauuucgag guucucgggg cccauccacu ugauuuuga uggcucugug    240 guagguggcg acuugcggug gguuugugaa gacagugaug gucagaguga agcuuaucga   300
uaccgucgac cucga                                                    315

<210> SEQ ID NO 8
<211> LENGTH: 99
<212> TYPE: RNA
<213> ORGANISM: Homo sapiens

<400> SEQUENCE: 8
ucgagguucu cggggcccau ccacugugau uuugauggcu cugugguagg uggcgacuug    60
cgguggguuu gugaagacag ugauggucag agugaagcu                           99

<210> SEQ ID NO 9
<211> LENGTH: 240
<212> TYPE: RNA
<213> ORGANISM: Homo sapiens

<400> SEQUENCE: 9
aacguugucg guguaaauga acugguucuu ggagcucccuu gaguaguugg gggaggugge   60 auguuggag gagucagccu agauugcguc uucacauccaa caggugaguc uggcauugug    120
gagugcuucu caguacgauu ucgagguucu cggggcccau ccacugugau uuugauggcu   180
cugugguagg uggcgacuug cgguggguuu gugaagacag ugauggucag agugaagcuu   240
```

<210> SEQ ID NO 10
<211> LENGTH: 21
<212> TYPE: DNA
<213> ORGANISM: Artificial sequence
<220> FEATURE:
<223> OTHER INFORMATION: siRNA probe
<220> FEATURE:
<221> NAME/KEY: misc_feature
<222> LOCATION: (20)..(21)
<223> OTHER INFORMATION: n is deoxythymidine

<400> SEQUENCE: 10
gcagaguuca aaagcccuun n                                              21

<210> SEQ ID NO 11
<211> LENGTH: 21
<212> TYPE: DNA
<213> ORGANISM: Artificial sequence
<220> FEATURE:
<223> OTHER INFORMATION: siRNA probe
<220> FEATURE:
<221> NAME/KEY: misc_feature
<222> LOCATION: (20)..(21)
<223> OTHER INFORMATION: n is deoxythymidine

<400> SEQUENCE: 11
aagggcuuuu gaacucugcn n                                              21

<210> SEQ ID NO 12
<211> LENGTH: 21
<212> TYPE: DNA
<213> ORGANISM: Artificial sequence
<220> FEATURE:
<223> OTHER INFORMATION: siRNA probe
<220> FEATURE:
<221> NAME/KEY: misc_feature
<222> LOCATION: (20)..(21)
<223> OTHER INFORMATION: n is deoxythymidine

<400> SEQUENCE: 12
agcagaguuc aaaagcccun n                                              21

<210> SEQ ID NO 13
<211> LENGTH: 21
<212> TYPE: DNA
<213> ORGANISM: Artificial sequence
<220> FEATURE:
<223> OTHER INFORMATION: siRNA probe
<220> FEATURE:
<221> NAME/KEY: misc_feature
<222> LOCATION: (20)..(21)
<223> OTHER INFORMATION: n is deoxythymidine

<400> SEQUENCE: 13
agggcuuuug aacucugcun n                                              21

<210> SEQ ID NO 14
<211> LENGTH: 40
<212> TYPE: RNA
<213> ORGANISM: Homo sapiens

<400> SEQUENCE: 14
uggauuuaag cagaguucaa aagcccuuca gcggccagua                          40

<210> SEQ ID NO 15
<211> LENGTH: 20
<212> TYPE: DNA
<213> ORGANISM: Artificial sequence -continued

```
<220> FEATURE:
<223> OTHER INFORMATION: primer

<400> SEQUENCE: 15
agcacggaca gactcatggg                                              20

<210> SEQ ID NO 16
<211> LENGTH: 20
<212> TYPE: DNA
<213> ORGANISM: Artificial sequence
<220> FEATURE:
<223> OTHER INFORMATION: primer

<400> SEQUENCE: 16
gctgccagtc tctgtcctgc                                              20

<210> SEQ ID NO 17
<211> LENGTH: 22
<212> TYPE: DNA
<213> ORGANISM: Artificial sequence
<220> FEATURE:
<223> OTHER INFORMATION: Taqman probe

<400> SEQUENCE: 17
agggccaggt ccagctggac cc                                           22

<210> SEQ ID NO 18
<211> LENGTH: 19
<212> TYPE: DNA
<213> ORGANISM: Artificial sequence
<220> FEATURE:
<223> OTHER INFORMATION: primer

<400> SEQUENCE: 18
ggctgtcctc gtcctccag                                               19

<210> SEQ ID NO 19
<211> LENGTH: 21
<212> TYPE: DNA
<213> ORGANISM: Artificial sequence
<220> FEATURE:
<223> OTHER INFORMATION: primer

<400> SEQUENCE: 19
tcagaccctg aggctcaaag t                                            21

<210> SEQ ID NO 20
<211> LENGTH: 24
<212> TYPE: DNA
<213> ORGANISM: Artificial sequence
<220> FEATURE:
<223> OTHER INFORMATION: Taqman probe

<400> SEQUENCE: 20
atctggaaga agcccttcag cggc                                         24
```

DOUBLE-STRANDED RNA (DSRNA) AND METHOD OF USE FOR INHIBITING EXPRESSION OF A FUSION GENE

RELATED APPLICATIONS

This application is a divisional application of U.S. patent application Ser. No. 10/349,320 filed on Jan 22, 2003, now U.S. Pat. No. 7,196,184, which claims priority to German Patent Application No. DE 102 02 419.7, filed Jan 22, 2002. The contents of these applications are incorporated herein by reference in their entirety.

BACKGROUND OF THE INVENTION

Chromosomal aberrations play a central role in the pathogenesis of many human malignant diseases, including hematologic neoplasms such as lymphoma and leukemia. Chromosomal abnormalities, characterized by structural changes or defects in one or more chromosomes, generally involve translocation, wherein a chromosome fragment is switched between non-homologous chromosomes; inversion, wherein the nucleotide sequence of a chromosome fragment is reversed; deletion (loss of a chromosomal fragment); insertion (incorporation of genetic material); duplication (repetition of an individual chromosome segment); or ring formation. These acquired genetic anomalies usually result in either activation of a quiescent gene or creation of a hybrid gene encoding a chimeric fusion oncoprotein, which triggers the malignant transformation. The chimeric fusion proteins created by cancer-associated chromosomal anomalies are ideal therapeutic targets because they are unique to the disease; they only exist in the malignant cells, not in the patient's normal cells (Cobaleda, C. et al., *Bioassays* (1995) 23:922).

A number of therapeutic agents which target expression of chimeric fusion genes are known in the art, including zinc-finger proteins (Choo, Y., et al. *Nature* (1994) 372:642), hammerhead-based ribozymes (James, H. A, and I. Gibson, *Blood* (1998) 91:371), and antisense RNA (Skorski, T. et al., *Proc. Natl. Acad. Sci. USA* (1994) 91:4504-4508). Each of these agents have inherent limitations. Zinc-finger proteins act at the DNA level, interacting with the target sequence and blocking transcription. However, gene fusions occur randomly and within introns, hence requiring a unique or "custom" zinc-finger for each patient. Antisense approaches, using either single-stranded RNA or DNA, act in a 1:1 stoichiometric relationship and thus have low efficacy, as well as questionable specificity (Skorsli et al., supra). Hammerhead ribozymes, which because of their catalytic activity can degrade a higher number of target molecules, have been used to overcome the stoichiometry problem associated with antisense RNA. However, hammerhead ribozymes require specific nucleotide sequences in the target gene, which are not always present.

More recently, double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (Hammond, S. M., et al., *Nature* (2000) 404:293-296). In other words, RNAi involves a catalytic-type reaction whereby new siRNAs are generated through successive cleavage of long dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi. WO 99/32619 (Fire et al.) discloses the use of a dsRNA of at least 25 nucleotides in length to inhibit the expression of a target gene in *C. elegans*. Sharp, P. A., *Genes & Dev.* (2001) 15:485-490, suggests that dsRNA from a related but not identical gene (i.e., >90% homologous) can be used for gene silencing if the dsRNA and target gene share segments of identical and uninterrupted sequences of significant length, i.e., more than 30-35 nucleotides. Unfortunately, the use of long dsRNAs in mammalian cells to elicit RNAi is usually not practical, due to the deleterious effects of the interferon response, as well as the inherent difficulties in delivering large molecules into a cell.

WO 00/44895 (Limmer, 2000) discloses the use of short dsRNA of less than 25 nucleotides (siRNA) for inhibiting expression of target genes in vertebrate cells. Similarly, WO 01/75164 A2 (Tuschl et al., 2001) discloses dsRNA of about 21 to 23 nucleotides for use in gene silencing by RNAi. Although the dsRNAs described in these references are small enough for intracellular delivery, neither reference suggests the use of siRNAs for inhibiting the expression of a chimeric fusion gene. Moreover, given the fact that chimeric fusion genes contain sequences from the cellular genes from which they originate, one would anticipate problems with specificity of inhibition, i.e., inhibition of both the chimeric fusion gene and the cellular genes. According to Sijen, T., et al., *Cell* (2001) 107:465-476, and Lipardi, C., et al., *Cell* (2001) 107:297-307, one strand of the siRNA would be elongated into a region that is complementary to the cellular genes. The new siRNAs formed by subsequent cleavage of the elongated products would have sequences that correspond exclusively to the cellular gene. Thus, one would anticipate inhibition of expression of the target gene as well as the cellular genes.

Finally, Cobaleda, I. and I. Sanchez-Garcia, *Blood* (2000) 95(3):731-737, discloses the use of a sequence-specific catalytic RNA subunit of RNase P from *E. coli* (MI RNA) to cleave target mRNA corresponding to the junction site in a bcr-abl fusion gene. However, the MI RNA approach suffers from the same deficiencies as the antisense approach, namely the potential for an interferon response and the inherent difficulties in delivering large molecules to cells. Moreover, because of its large size, production of therapeutic or commercial amounts of MI RNA cannot reasonably be accomplished using solid-phase synthesis. Instead, MI RNA must be prepared through enzymatic synthesis, which is costly.

Thus, despite significant advances in the field, there remains a need for agents that target expression of chimeric fusion genes associated with chromosomal aberrations. In particular, agents that are small enough for efficient intracellular delivery, and which have both high efficacy (hence are effective at low dosages) and high specificity for the target fusion gene would be therapeutically beneficial. Such agents would be useful for treating diseases caused by chromosomal anomalies, particularly malignant diseases such as lymphoma and leukemia.

SUMMARY OF THE INVENTION

The present invention discloses a short double stranded RNA (dsRNA) that specifically inhibits the expression of fusion genes in mammals. The dsRNA may be approximately 19-24 nucleotides in length, and have a nucleotide sequence that is complementary to at least a part of the target gene that contains a fusion site.

In one aspect, the dsRNA of the invention contains a first complementary RNA strand and a second RNA strand. The first complementary RNA strand has a corresponding nucleotide sequence of between about 20-23 nucleotides, which is complementary to an mRNA transcript of a portion of the target gene containing a fusion site. The first complementary RNA strand and the second RNA strand of the dsRNA both have a 3'-terminus and a 5'-terminus. The nucleotide sequence of the dsRNA may be about 22 nucleotides in length. The nucleotide sequence of the dsRNA may also contain at least two nucleotides on each side of the fusion site that are complementary to the corresponding nucleotides on either side of the fusion site of the target gene. At least one of the RNA strands of the dsRNA may have a nucleotide overhang of between about one and about four nucleotides in length. The nucleotide overhang may be one or two nucleotides in length. At least one of the RNA strands of the dsRNA may have a nucleotide overhang on the 3'-terminus. Only one of the RNA strands may have a nucleotide overhang, and the overhang may be on the 3'-terminus of the first complementary RNA strand. At least one of the ends of the dsRNA may also have a linker between the first complementary RNA strand and the second RNA strand. The linker may be a chemical linker such as a hexaethylene glycol linker that links the 5'-terminus of the first complementary RNA strand with the 3'-terminus of the second RNA strand.

In one aspect of the invention, the target gene comprises an AML-1/MTG8 fusion site. The first complementary RNA strand may have a nucleotide sequence of SEQ. ID NO:1 and the second RNA strand may have a nucleotide sequence of SEQ. ID NO:2.

In another aspect of the invention, the ribonucleic acid (RNA) may have a double stranded structure that comprises a single-self complementary RNA strand having a nucleotide sequence of between about 19 and about 24 nucleotides in length, which is substantially identical to at least a part of a target gene with a fusion site in a mammalian cell. The dsRNA may contain a 3'-terminus and a 5'-terminus and the double stranded structure may contain a first end and a second end. The first end comprises a loop structure and the second end comprises the 3'-terminus and the 5'-terminus and a nucleotide overhang of between about one and about four nucleotides in length. In a further aspect, the overhang may be one or two nucleotides in length and be located on the 3'-terminus.

In another aspect, the invention relates to a method for inhibiting the expression of a target gene in a mammalian cell. The method involves introducing a dsRNA of the invention into a cell. The dsRNA comprises a double stranded structure having a nucleotide sequence of between 19 and 24 nucleotides in length, which is substantially identical to at least a part of a target gene with a fusion site in the mammalian cell. The method further involves maintaining the cell under conditions, and for a time sufficient to obtain degradation of mRNA of the target gene and inhibition of the expression of the target gene in the cell.

In a further aspect, the invention provides for a method of inhibiting the expression of a target gene in a mammalian cell using a dsRNA comprising a first complementary RNA strand, containing a corresponding nucleotide sequence, which is complementary to a mRNA transcript of a portion of the target gene and a second RNA strand. The first complementary RNA strand and the second RNA strand comprise a 3'-terminus and a 5'-terminus and may have a sequence of between about 20 and about 23 nucleotides in length. In one embodiment, the nucleotide sequence may be about 22 nucleotides in length. In another embodiment, the nucleotide sequence comprises at least two nucleotides on each side of a corresponding fusion site and the fusion site is complementary to the corresponding fusion site of the target gene. The nucleotide sequence of the RNA may also comprise at least three nucleotides on each side of the corresponding fusion site. In one embodiment, at least one of said RNA strands comprises a nucleotide overhang of between about one and about four nucleotides in length. In one embodiment, at least one of the RNA strands has a nucleotide overhang on the 3'-terminus. In one embodiment, only the first complementary RNA strand has a nucleotide overhang, and the overhang is on the 3'-terminus of the first complementary RNA strand. At least one of the ends of the dsRNA may comprise a chemical linker, such as a hexaethylene glycol linker. The linker may connect the 5'-terminus of the first complementary RNA strand and the 3'-terminus of the second RNA strand. The target gene may comprise an AML-1/MTG8 fusion site. The first complementary RNA strand of the dsRNA may have the nucleotide sequence of SEQ. ID NO: 1; and the second RNA strand may have the nucleotide sequence of SEQ. ID NO:2. Alternatively, the target gene may comprise a bcr/ab 1 fusion site, or any other known fusion site resulting from a chromosomal aberration, including BCL-1/IgH, TAL-1, TCR, TAL-1/SIL, c-MYC/IgH, cMYC/IgL, MUM1/RF4, MUM1/IgH, RAX-5/BSAP, MLL/HRX, E2A/PBX, E2A/HLF, NPM/ALK, and NPM/MLF1. The mammalian cell may be a leucocyte or a myelogenic cell. The target gene may result from a chromosomal aberration. In one embodiment, the target gene causes, or is likely to cause, disease. The dsRNAs of the present invention are useful for treating diseases caused by chromosomal aberrations, particularly malignant diseases such as lymphoma ad leukemia. The RNA may be produced by chemical synthesis or by an expression vector in the cell. In one embodiment, the nucleotide sequence has at least 90% identity with the target gene.

In another aspect, the invention provides for a method for treating a mammal having a disease caused by the expression of a fusion gene, which results from a chromosomal aberration, by administering to the mammal an RNA that inhibits the expression of the target gene. The RNA comprises a double stranded structure having a nucleotide sequence, which is substantially identical to at least a part of a target gene and a nucleotide sequence of between about 19 and about 24 nucleotides in length. In one embodiment, the RNA comprises a first complementary RNA strand and a second RNA strand, wherein the first complimentary RNA strand corresponding nucleotide sequence, which is complementary to an mRNA transcript of a portion of the target gene, and the first complementary RNA strand and the second RNA strand comprise a 3'-terminus and a 5'-terminus. In another embodiment, the nucleotide sequence may be between about 20 and about 23 nucleotides in length. In another embodiment, the target gene may comprise a fusion site, and the nucleotide sequence of the dsRNA may comprise at least two nucleotides on each side of the fusion site within the target gene. In another embodiment, at least one of said RNA strands may have a nucleotide overhang of between about one and about four nucleotides in length. In another embodiment, the first complementary RNA strand has a nucleotide overhang on the 3'-terminus. In another embodiment, at least one of the ends may have a linker, such as hexaethylene glycol, between the first complementary RNA strand and the second RNA strand. In a further aspect, the target gene may be an AML/MTG8 fusion gene, a BCR/ABL fusion gene or a target gene selected from the group of fusion genes consisting of BCL-1/IgH, TAL-1/TCR, TAL-1/SIL, c-MYC/IgH, c-MYC/IgL, MUM1/RF4, MUM/IgH, RAX-5/BSAP, MLL/HRX, E2A/PBX, E2A?HLF, NPM/ALK, and NPM/MLF1. The target gene may be a result of a chromosomal aberration, which causes, or is likely to cause a disease, for example, acute myelogenous leukemia.

In another aspect, the invention provides for a method of using an RNA to inhibit the expression of target gene with a fusion site in a mammalian cell. According to the invention, the RNA may be about 19 to 24 nucleotides in length and comprise a double stranded structure, having a nucleotide sequence that is substantially identical to at least a part of a target gene with a fusion site in the mammalian cell.

In further aspect, the invention relates to a pharmaceutical composition comprising the dsRNA of the invention and pharmaceutically acceptable carrier. The dsRNA may have a double stranded structure and a nucleotide sequence, of between about 19 and about 24 nucleotides in length, which is substantially identical to at least a part of a target gene with a fusion site in the mammalian cell. In another aspect, the mammalian cell may be a leukocyte or a myelogenic cell. The target gene may be result of a chromosomal aberration, which causes or is likely to cause a disease such as leukemia or lymphoma.

DETAILED DESCRIPTION OF THE INVENTION

Figure 1:
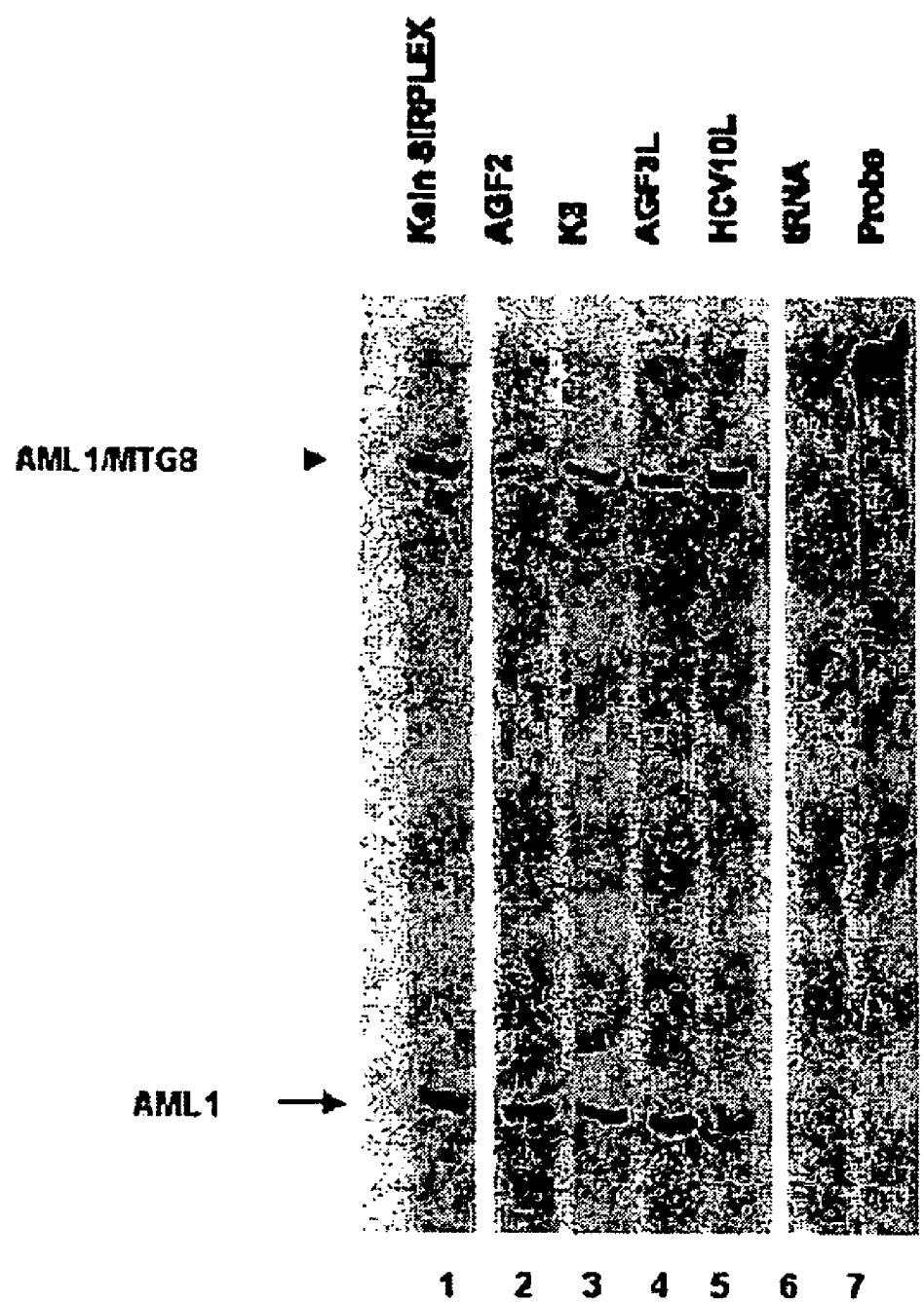
FIG. 1 is an autoradiograph of RNase protection assays of cellular RNAs performed 20 hours after electroporation of Kasumi-1 cells with 200 nM siRNA. Protected fragments corresponding to AML-1/MTG8 having 240 nucleotides in length and to AML-1 having 100 nucleotides in length are indicated on the left. The electroporated siRNAs are indicated at the top of Lanes 1 to 5. Lane 6 shows a transfer RNA (tRNA) control to monitor completeness of digestion; Lane 7 represents the undigested 315-nucleotide probe.

The present invention relates to the specific inhibition of expression of a fusion gene in a mammal using a short double stranded RNA (dsRNA). dsRNA directs the sequence-specific degradation of mRNA through a process known as RNA interference (RNAi). The process occurs in a wide variety of organisms, including mammals and other vertebrates. Using a mammalian tissue cell culture, the present inventors have demonstrated that dsRNA of approximately 19-24 nucleotides, preferably 20-23 nucleotides, and most preferably 22 nucleotides in length, which have a nucleotide sequence complementary to a target fusion gene, can specifically and efficiently mediate RNAi. The present invention encompasses these short dsRNAs and their use for specifically inactivating gene function. The use of these dsRNAs enables the targeting of mRNAs of fusion genes resulting from a chromosomal aberration. Thus, the dsRNAs of the present invention are useful for treating diseases caused by chromosomal aberrations, particularly malignant diseases such as lymphoma and leukemia.

The dsRNA of the present invention comprise a double stranded structure, and have a nucleotide sequence which is substantially identical to at least a part of the target gene. "Identity," as known in the art, is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M stockton Press, New York (1991)). Methods commonly employed to determine identity between sequences include, for example, those disclosed in Carillo, H., and Lipman, D., *SIAM J. Applied Math*. (1988) 48:1073. "Substantially identical," as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene, provided that the mismatches occur at a distance of at least three nucleotides from the fusion site.

As used herein, "target gene" refers to a section of a DNA strand of a double-stranded DNA that is complementary to a section of a DNA strand, including all transcribed regions, that serves as a template for transcription. The target gene is therefore usually the same sense strand. As used herein, "gene" refers to a region in DNA, bounded by an initiation (start) site and termination site, that is transcribed into a single primary transcript. As used herein, "cellular gene" refers to a gene present in a cell or organism.

The term "complementary RNA strand" refers to the strand of the dsRNA which is complementary to an mRNA transcript that is formed during expression of the target gene, or its processing products. "dsRNA" refers to a ribonucleic acid molecule having a duplex structure comprising two complementary and anti-parallel nucleic acid strands. Not all nucleotides of a dsRNA must exhibit Watson-Crick base pairs. The maximum number of base pairs is the number of nucleotides in the shortest strand of the dsRNA.

As used herein, "fusion site" refers to a site on a target gene where at least two cellular genes, which are normally present at distinct locations on the chromosome or on different chromosomes, are joined as a result of a chromosomal aberration. "Chromosomal aberrations" or "chromosomal abnormalities," which are characterized by structural changes or defects in one or more chromosomes, generally involve translocation, wherein a chromosome fragment is switched between non-homologous chromosomes. Chromosomal aberration can also be caused by other acquired genetic alterations, including inversion (wherein the nucleotide sequence of a chromosome fragment is reversed), deletion (loss of a chromosomal fragment), insertion (incorporation of genetic material), duplication (repetition of an individual chromosome segment), and ring formation.

The term "corresponding fusion site," as used herein, refers to a fusion site in the nucleotide sequence of an RNA strand of the dsRNA that is complementary to the fusion site of the target gene. A dsRNA "comprises" a fusion site when at least one nucleotide is present on one side of the fusion site. The remainder of the complementary strand comprises nucleotides on the opposite side of the corresponding fusion site. Thus, the fusion site is not located entirely at the beginning or end of the complementary segment of the RNA strand. The complementary segment of the RNA strand preferably comprises at least 16 nucleotides. "Introducing into" means uptake or absorption in the cell, as is understood by those skilled in the art. Absorption or uptake can occur through cellular processes, or by auxiliary agents or devices.

In one embodiment, the invention relates to an RNA having a double-stranded structure and a nucleotide sequence which is substantially identical to at least a part of the target gene, which comprises the fusion site. The RNA is between about 19 and about 24 nucleotides in length. The dsRNA comprises two complementary RNA strands, one of which comprises a nucleotide sequence which is substantially identical to a portion of the target gene. Preferably, the nucleotide sequence of the RNA which contains the corresponding fusion site has at least three nucleotides on each side of the fusion site. For example, a sequence of 21 nucleotides in length would have at least three nucleotides on one side of the corresponding fusion site, and up to 18 nucleotides on the opposite side of the fusion site. Surprisingly, the present inventors have discovered that dsRNAs having this nucleotide configuration demonstrate exceptional efficiency and specificity of activity.

In a preferred embodiment, at least one end of the dsRNA has a single-stranded nucleotide overhang of between one and four, preferably one or two nucleotides. As used herein, a "nucleotide overhang" refers to the unpaired nucleotide or nucleotides that protrude from the duplex structure when the 5'-terminal end of one RNA strand extends beyond the 3'-terminus end of the other strand, or vice versa. dsRNAs having at least one nucleotide overhang have unexpectedly superior inhibitory properties than their blunt-ended counterparts. Moreover, the present inventors have discovered that the presence of one nucleotide overhang strengthens the interference activity of dsRNA, without diminishing the overall stability of the structure, as typically happens with dsRNA having nucleotide overhangs at both ends. dsRNA having only one overhang has proven particularly stable and effective in a variety of cells and cell culture mediums, as well as in blood and serum. Preferably, the single-stranded overhang is located at the 3'-terminal end of the complementary RNA strand (also referred to herein as the "S1" strand). Such a configuration produces a further increase in efficiency.

The nucleotide sequence on the complementary RNA strand (S1 strand) preferably has between 20 and 23 nucleotides, most preferably 22 nucleotides. Such dsRNA are particularly robust gene silencers. The complementary RNA strand of the dsRNA strand preferably has fewer than 30 nucleotides, more preferably fewer than 25 nucleotides, and most preferably 21 to 24 nucleotides. Such dsRNA exhibit superior intracellular stability.

At least one end of the dsRNA may be modified to improve resistance to degradation and/or dissociation of the two strands of the duplex. Furthermore, the cohesiveness of the double-stranded stricture formed by base pairing between the complementary RNA strands can be further improved by the presence of one, and preferably two, chemical linkages. Chemical linking may be achieved by any of a variety of well-known techniques, including through covalent, ionic or hydrogen bonds; hydrophobic interactions, preferably van der Waals or stacking interactions; or by means of metal-ion coordination. The purines of the dsRNA may also be replaced with purine analogues. Most preferably, the chemical linkage is achieved using a hexa-ethylene glycol linker on one end of the dsRNA. In a preferred embodiment, the linkage is formed between the 5'-terminus of the complementary RNA strand and the 3'-terminus of the second RNA strand.

In another embodiment, the present invention relates to a method for inhibiting the expression of a target gene comprising a fusion site using a dsRNA. The method comprises introducing a dsRNA having a nucleotide sequence which is substantially identical to at least a part of a target gene into a mammalian cell. The RNA is preferably between 20 and 23 nucleotides in length, most preferably 22 nucleotides. The resulting cell is maintained under conditions and for a time sufficient to achieve degradation of mRNA of the target gene, thereby silencing expression of the target gene.

In still another embodiment, the invention relates to a method for treating a mammal having a disease caused by the expression of a fusion gene which results from a chromosomal aberration. The method comprising administering the dsRNA of the invention to the animal, such that expression of the target fusion gene is silenced. Because of their surprisingly improved specificity, the dsRNAs of the present invention specifically target mRNAs of chimeric fusion genes of diseased cells and tissues, without affecting the surrounding normal cells. Thus, the dsRNAs of the present invention are particularly useful for treating diseases caused by chromosomal aberrations, particularly malignant diseases such as lymphoma and leukemia.

Examples of diseases which can be treated using the dsRNA of the invention include, without limitation, acute myelogenous leukemias (AML), chronic myelogenous leukemias (CML), mantle cell lymphoma, follicular lymphoma, diffuse large B-cell lymphoma, T-cell acute lymphoblastic leukemia, Burkett lymphoma, myeloma, immunocytoma, acute promyelocytic leukemia, chronic myeloid/acute lymphoblastic leukemia, acute leukemia, B-cell acute lymphoblastic leukemia, anaplastic large cell lymphoma, and myelodysplastic syndrome/acute mycloid leukemia. These leukemias and lymphomas can be treating using a dsRNA specifically designed to inhibit expression of the aberrant fusion gene. Although the present examples describe the preparation of dsRNAs which target the AML-1/MTG8 and bcr/abl fusion genes, other dsRNAs can be constructed to target other fusion genes using well-known techniques and by following the teachings of the present invention. Examples of other fusion genes which can be used in the methods of the invention include, without limitation, BCL-1/IgH, TAL-1/TCR, TAL-1/SIL, c-MYC/IgH, c-MYC/IgL, MUM1/RF4, MUM1/IgH, RAX-5/BSAP, MLL/HRX, E2A/PBX, E2A/HLF, NPM/ALK, and NPM/MLF1.

Acute myelogenous leukemias (AML) are heterogeneous, malignant diseases of the hemopoietic system. AML is caused by expression of an aberrant fusion gene, which results in loss of the ability of the cell to differentiate, while retaining the potential to proliferate. This leads to the promulgation of a malignant cell clone, with resultant suppression of normal hematopoiesis. Untreated, AML causes death, usually within a few weeks. The incidence of AML is age-dependent, rising from 1/100,000 in persons under 30 years of age to 14/100,000 in persons over 70.

As many as 90% of cases of adult AML demonstrate chromosomal aberrations. One of the most frequent aberrations is the t(8;21) (q22;q22) translocation, which occurs in 10-15% of all AML cases. In this translocation, the AML-1 transcription factor, which is essential for hematopoiesis, is fused with the MTG8 transcription repressor. The resulting fusion protein (AML-1/MTG8) contains almost the entire MTG8 sequence instead of the C-terminal transactivation domain of AML-1. Expression of this faulty gene results in inhibition of cell differentiation in CD34-positive cells, as well as initiation of leukemic transformation in the affected cells.

In an exemplified embodiment, the target gene comprises an AML-1/MTG8 fusion gene. In this example, the complementary RNA (S1) strand of the dsRNA has the sequence set forth in SEQ ID NO: 1, and the second (S2) strand has the sequence of SEQ ID NO:2. Such a construct is useful for treating either acute myelogenic leukemia or chronic myelogenic leukemia. As described in more detail below, the dsRNA can be administered using any acceptable carrier, including buffer solutions, liposomes, micellar structures, and capsids, the latter two of which facilitate intracellular uptake of dsRNA. Although the therapeutic agent can be administered by a variety of well known techniques, again as discussed below, presently preferred routes of administration include inhalation, oral ingestion, and injection, particularly intravenous or intraperitoneal injection, or injection directly into the affected bone marrow. An example of a preparation suitable for inhalation or injection is a simple solution comprising the dsRNA and a physiologically tolerated buffer, particularly a phosphate buffered saline solution.

In yet another embodiment, the invention relates to a pharmaceutical composition for treating a disease caused by a chromosomal aberration. In this aspect of the invention, the dsRNA of the invention is formulated as described below. The pharmaceutical composition is administered in a dosage sufficient to inhibit expression of the target gene. The present inventors have found that compositions comprising the dsRNA can be administered at a unexpectedly low dosages. Surprisingly, a dosage of 5 mg dsRNA per kilogram body weight per day is sufficient to inhibit or completely suppress expression of the target gene. Furthermore, the pharmaceutical composition is highly specific in inhibiting expression of the target gene, without affecting expression of the individual cellular genes from which the fusion gene originated. Because of the high specificity of these dsRNA and low dosage requirements, side effects are either minimal or nonexistent.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease of disorder is the amount necessary to effect that at least 25% reduction.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired the tablets may be coated with a material such as glyceryl monostearate or glyceryl distearate, to delay absorption in the gastrointestinal tract.

The dsRNAs encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration.

For oral administration, the dsRNAs useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the dsRNAs of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The dsRNAS useful according to the invention may also be presented as liposome formulations.

In general a suitable dose will be in the range of 0.01 to 100 mg per kilogram body weight of the recipient per day, preferably in the range of 0.2 to 10 mg per kilogram body weight per day, and most preferably about 5 mg per kilogram body weight per day. The desired dose is preferably presented once daily, but may be dosed as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Dosages useful according to the invention will vary depending upon the condition to be treated or prevented and on the identity of the inhibitor being used. Estimates of effective dosages and in vivo half-lives for the individual dsRNAs encompassed by the invention can be made on the basis of in vivo testing using an animal model, such as a mouse model for lematological malignancies.

Advances in mouse genetics have generated a number of mouse models for the study of hematopoietic malignancies including leukemias, lymphomas and acute myelogenous leukemia. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov) as well as the NCI-MMHCC mouse repository. Examples of the genetic tools that are currently available for the modeling of leukemia and lymphomas in mice, and which are useful in practicing the present invention, are described in the following references: Bernardi, R., et al. (2002), "Modelling haematopoietic malignancies in the mouse and clinical implications," *Oncogene* 21, 3445-3458; Maru, Y. (2001), Molecular biology of chronic myeloid leukemia, *Int. J. Hematol.*, 73, 308-322; Pandolfi, P. P. (2001), In vivo analysis of the molecular genetics of acute promyelocytic leukemia, *Oncogene* 20, 5726-5735; Pollock, J. L., et al. (2001) Mouse models of acute promyelocytic leukemia, *Curr. Opin. Hematol.* 8, 206-211; Rego, E. M., et al. (2001) Analysis of the molecular genetics of acute promyelocytic leukemia in mouse models, *Semin. in Hemat.* 38, 54-70; Shannon, K. M., et al. (2001) Modeling myeloid leukemia tumors suppressor gene inactivation in the mouse, *Semin. Cancer Biol.* 11, 191-200; Van Etten, R. A., (2001) Pathogenesis and treatment of Ph+ leukemia: recent insights from mouse models, *Curr. Opin. Hematol.* 8, 224-230; Wong, S., et al. (2001) Modeling Philadelphia chromosome positive leukemias, *Oncogene* 20, 5644-5659; Higuchi M et al. (2002) Expression of a conditional AML1-ETO oncogene bypasses embryonic lethality and establishes a murine model of human t(8;21) acute myeloid leukemia, *Cancer Cell* 1(1):63-74; Bichi, R. et al. (2002) Human chronic lymphocytic leukemia modeled in mouse by targeted TCL1 expression, *Proc. Natl. Acad. Sci. USA*, Vol. 99, Issue 10, 6955-6960; Phillips J A. Et al. (1992) The NZB mouse as a model for chronic lymphocytic leukemia, *Cancer Res.* 52(2):437-43; Harris A W et al. (1988) The E mu-myc transgenic mouse. A model for high-incidence spontaneous lymphoma and leukemia of early B cells, *J Exp Med.* 167(2):353-71; Zeng X X et al. (1998) The fetal origin of B-precursor leukemia in the E-mu-ret mouse, *Blood.* 92(10):3529-36; Eriksson B et al. (1999) Establishment and characterization of a mouse strain (TLL) that spontaneously develops T-cell lymphomas/leukemia, *Exp Hematol.* 27(4): 682-8; and Kovalchuk A. et al. (2000) Burkitt lymphoma in the mouse, *J Exp Med.* 192(8): 1183-90. Mouse repositories can also be found at: The Jackson Laboratory, Charles River Laboratories, Taconic, Harlan, Mutant Mouse Regional Resource Centers (NMRRC) National Network and at the European Mouse Mutant Archive.

In addition to their administration singly, the dsRNAs useful according to the invention can be administered in combination with other known agents effective in treatment of malignant diseases. In any event, the administering physician can adjust the amount and timing of dsRNA administration on the basis of results observed using standard measures of efficacy known in the art or described herein.

The present invention is illustrated by the following examples, which are not intended to be limiting in any way.

EXAMPLES

Example 1

Inhibition of AML-1/TG8 Fusion Gene Expression by RNA Interference

In this Example, AML-1/MTG8 double stranded siRNAs transfected into Kasumi-1 tissue culture cells are shown to specifically inhibit AML-1/MTG8 fusion gene expression.

Synthesis and Preparation of dsRNAs

Oligoribonucleotides were synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM tris, 10 mM NaClO$_4$, pH 6.8, 10% acetonitrile; flow rate: 3 ml/min). Formation of double stranded siRNAs was then achieved by heating a stoichiometric mixture of the individual complementary strands (10 M) to 95° C. for 5 minutes in 25 mM tris-HCl, pH 7.5, and 100 mM NaCl, followed by subsequent cooling for 30 minutes to 37° C.

dsRNA molecules with linkers were produced by solid phase synthesis and addition of hexaethylene glycol as a non-nucleotide linker (D. Jeremy Williams, Kathleen B. Hall, Biochemistry 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) was coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite was comparable to the incorporation of nucleoside phosphoramidites.

Two dsRNAs (AGF2 and AGF-3) were generated that target the sequences immediately adjacent to the site where the AML-1 gene is fused to the MTG8 gene. K3 and HCV10L dsRNAs were used as internal controls. The sequences of the respective dsRNAs (SEQ ID Nos. 1-6) are depicted below:

AGF2 dsRNA:

```
S2:  5'-CCUCGAAAUCGUACUGAGAAG-3'     (SEQ ID NO: 2)
S1*: 3'-UUGGAGCUUUAGCAUGACUCUUC-5'   (SEQ ID NO: 1)
```

The S1 strand is complementary to the coding strand of the AML-1/MGTG8 fusion gene. Underlined sequences correspond to MTG8 gene sequences whereas the sequences that are not underlined correspond to AML-1 gene sequences.

AGF3L dsRNA:

```
S2: 5'-CCUCGAAAUCGUACUGAGAAG         (SEQ ID NO: 2)
                              \
                              Linker*
                              /
S1: 3'-UUGGAGCUUUAGCAUGACUCUUC        (SEQ ID NO: 1)
```

AGF3L dsRNA has the same sequence as AGF2 dsRNA but, in addition, includes a hexaethylene glycol linker (*) that joins the 5'-end of the S1 strand to the 3'-end of the S2 strand. Underlined sequences correspond to MTG8 gene sequences whereas the sequences that are not underlined correspond to AML-1 gene sequences.

K3 dsRNA: the S1 strand is complementary to a sequence of the 5'-untranslated region of a neomycin resistance gene:

```
S2: 5'-GAUGAGGAUCGUUUCGCAUGA-3'     (SEQ ID NO: 4)
S1: 3'-UCCUACUCCUAGCAAAGCGUACU-5'   (SEQ ID NO: 3)
```

HCV10L dsRNA: the S1 strand is complementary to a sequence of the HCV gene. A hexaethylene glycol linker (*) joins the 5'-end of the S1 strand to the 3'-end of the S2 strand:

```
S2 5'-ACGGCUAGCUGUGAAAGGUCC          (SEQ ID NO: 6)
                             \
                             Linker*
                             /
S1 3'-AGUGCCGAUCGACACUUUCCAGG        (SEQ ID NO: 5)
```

Transfection of dsRNAs into Kasuni-1 Cells

The Kasumi-1 cell line (Asou, H. et al. [1991] Blood 77, 2031-2000 36), harbors a t(8;21) translocation by which the AML-1 gene is fused to the MTG-1 gene.

The dsRNAs described above were transfected into these cells using the following protocol. DsRNAs were first added to $10^6$ cells in 100 μl RPMI1640 with 10% FCS to a final concentration of 200 nM and then electroporated in a 0.4 cm-wide electroporation cuvette at 300 V for 10 minutes using a Fischer Electroporator (Fischer, Heidelberg). After a 15-minute incubation at room temperature, the cell suspension was transferred to 2 ml RPMI164' with 10% fetal calf serum, and incubated a further 20 hours at 37° C., 5% $CO_2$, and 95% humidity prior to processing and analysis.

RNA Purification and Analysis

Cytoplasmic RNA was purified with the help of the RNeasy Kit (Qiagen, Hilden) and analyzed using a RNase protection assay as previously described (Ausubel, F. M., Brent, R., Kingston, R. E., Moore, D. D., Seidman, J. G., Smith, J. A., and Strul, K. (1993) Current Protocols in Molecular Biology, Greene and Wiley, New York, N.Y.). The following modifications were included: the hybridization volume was reduced to 15 μl, the hybridization temperature was 60° C., and the RNase digestion was performed in a total volume of 175 μl.

SEQ ID NO: 7 represents the sequence of the RNA probe. Sequences protected by AML1/MTG8-mRNA are in lower case, sequences protected by AML1-mRNA are in bold:

```
5'-GGGCGAAUUG GAGCUCCACC GCGGUGGCGG CCGCUCUAGA

ACUAGUGGAUCCCCCaacgu gucggugua aaugaacugg uucuuggagc uccuugagua guuggggag guggcauugu uggaggaguc agccuagauu gcgucuucac auccacaggu gagucuggca uuguggagug cuucucagua cgauuucgag guucucgggg cccauccacu gugauuuuga uggcucugug guagguggcg acuugcggug ggauuugugaa gacgugaug gucagaguga agcuuAUCGA UACCGUCGAC CUCGA-3'

(SEQ. ID NO: 7)
```

Sequence of the 100 nucleotide fragment protected by the AML-1 mRNA is:

```
                                    (SEQ ID NO: 8)
5'-UCGAGGUUCU CGGGGCCCAU CCACUGUGAU UUUGAUGGCU

CUGUGGUAGG UGGCGACUUG CGGUGGGUUU GUGAAGACAG

UGAUGGUCAG AGUGAAGCUU-3'
```

Sequence of the 240 nucleotide fragment protected by the AML-1/MTG8 fusion mRNA is:

```
                                    (SEQ ID NO: 9)
5'-AACGUUGUCG GUGUAAAUGA ACUGGUUCUU GGAGCUCCUU

GAGUAGUUGG GGGAGGUGGC AUUGUUGGAG GAGUCAGCCU

AGAUUGCGUC UUCACAUCCA CAGGUGAGUC UGGCAUUGUG

GAGUGCUUCU CAGUACGAUU UCGAGGUUCU CGGGGCCCAU

CCACUGUGAU UUUGAUGGCU CUGUGGUAGG UGGCGACUUG

CGGUGGGUUU GUGAAGACAG UGAUGGUCAG AGUGAAGCUU-3'
```

After RNase treatment, the RNA was analyzed by polyacrylamide gel electrophoresis under denaturing conditions (see FIG. 1) and the relative amount of different RNAase resistant fragments was quantitated by phosphor imaging. As can be seen in FIG. 1, the identity of the transfected dsRNAs is indicated above each lane. Lane 1 shows the cytoplasmic RNA from a cell that was electroporated in the absence of a dsRNA. A 315-nucleotide long RNA that is complementary to the AML-1/MTG8 fusion site was used as the undigested sample RNA (FIG. 1, Lane 7). The denaturing temperature was 95° C., the hybridization temperature 60° C. Conditions for complete digestion were tested using tRNA (FIG. 1, Lane 6).

Figure 2:
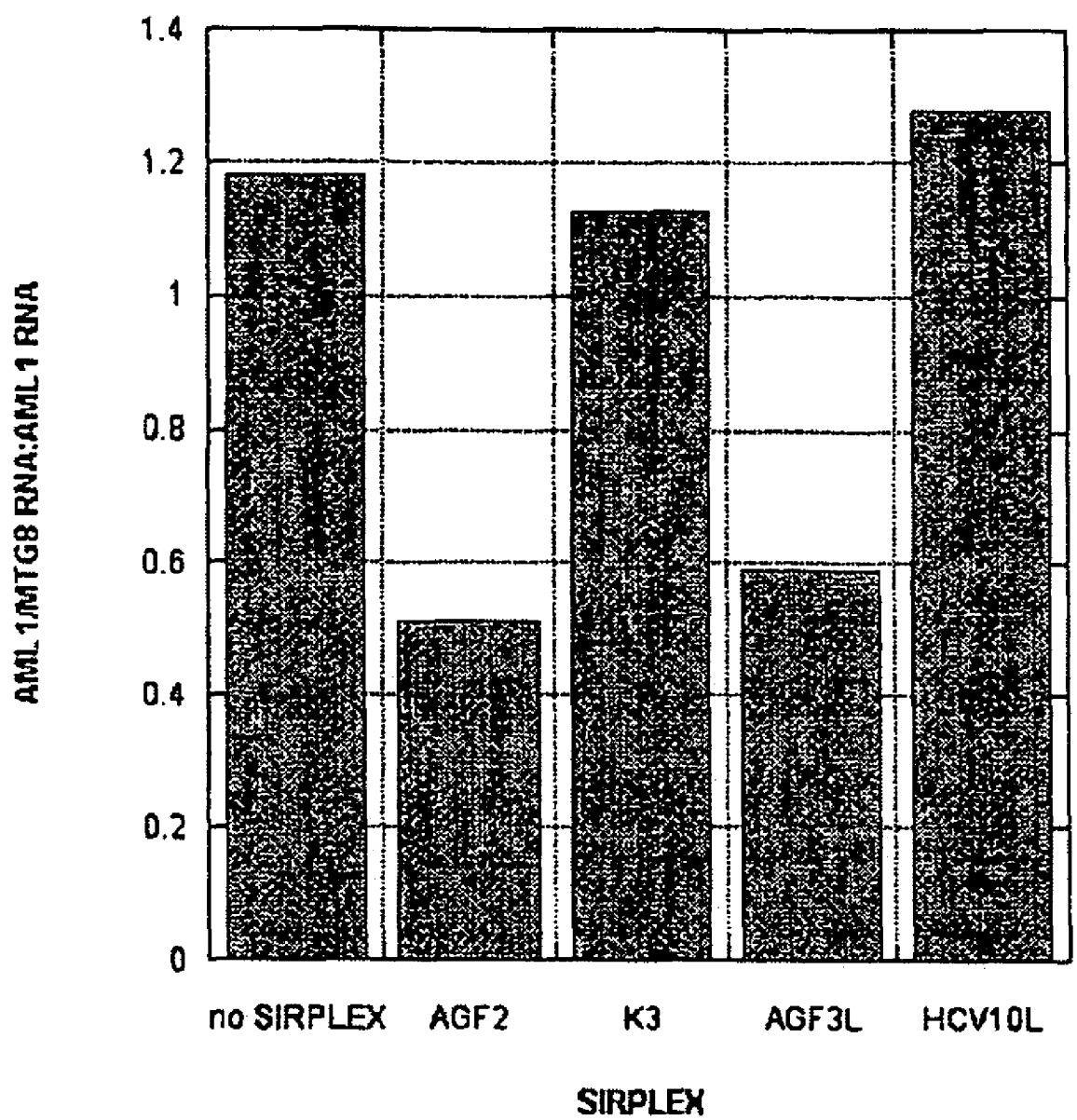
FIG. 2 is a graphic representation of the ratios between AML-1/MTG8 and AML-1 intensities. Band intensities from the experiment in FIG. 1 were quantified by phosphoimaging and the relative ratios of AML-1/MRG8 mRNA to AML-1 mRNA was determined. Electroporated siRNAs are indicated at the bottom.

Both AML-1/MTG8-specific fragments having a length of 240 nucleotides as well as AML-1-specific fragments having a length of 100 nucleotides were seen in all assays (see arrows, FIG. 1). Bands corresponding to 91 nucleotide long fragments result from the expression of the untranslocated wild type allele. Neither the control-nor the AML-1/MTG8-specific dsRNAs reduced the AML-1 signal of non-fused mRNA (FIG. 1, compare lane 1 with lanes 3 and 5). In contrast to the control dsRNAs (K3 and HCV10L; FIG. 1, lanes 3 and 5), both AML-1/MTG8 fusion mRNA specific dsRNAs: AGF2 dsRNA, in which both strands are non linked (see FIG. 1, lane 2) and AGF3L dsRNA (in which both strands are linked by a hexaethylene glycol linker (see FIG. 1, lane 4)), reduced the AML-1/MTG8 signal significantly. Whereas the ratio of the AML-1/MTG8 to AML-1 signal fluctuates between 1.1 and 1.4 both in cells that were electroporated in the absence of dsRNAs and in cells that were transfected with control dsRNAs, electroporation in the presence of AML-1/MTG8-specific dsRNAs resulted in a significant reduction in this ratio to between 0.4 and 0.6 (FIG. 2). Thus, AML-1/MTG8-specific dsRNAs containing a hexaethylene glycol linker can specifically reduce expression of the AML-1/MTG8 fusion gene to 46% of the expression seen in the absence of AML-1/MTG8-specific dsRNAs, whereas the expression of the untranslocated allele remained unaltered either in the presence or absence of dsRNAs. Assuming an electroporation efficiency of 50%, these results indicate that transfected AML-1/MTG8-specific dsRNAs are highly effective at specifically targeting and degrading AML-1/MTG8 fusion gene transcripts.

Example 2

Inhibition of Bcr-Abl Fusion Gene Expression by RNA Interference

In this Example, Bcr-Abl-specific double stranded siRNAs transfected into CD34+ primary hematopoietic cells from CML patients are shown to specifically inhibit Bcr-Abl gene expression.

SiRNA Synthesis 21-nt single-stranded RNAs (BCR-ABL-1 and BCR-ABL-2) directed against the fusion sequence of bcr-abl are chemically synthesized with or without a hexaethylene glycol linker as described in Example 1.

The sense and antisense sequences of the siRNAs are:

```
BCR-ABL-1:    5'-GCAGAGUUCAAAAGCCCUUdTdT-3' (s1)
              (SEQ. ID NO: 10)
              5'-AAGGGCUUUUGAACUCUGCdTdT-3' (s2)
              (SEQ. ID NO: 11)

BCR-ABL-2:    5'-AGCAGAGUUCAAAAGCCCUUdTdT-3' (s1)
              (SEQ. ID NO: 12)
              5'-AGGGCUUUUGAACUCUGCUdTdT-3' (s2)
              (SEQ. ID NO: 13)

↓bcr-abl
5'...UGGAUUUAAGCAGAGUUCAAAAGCCCUUCAGCGGCCAGUA...3'
  (SEQ. ID NO: 14)

BCR-ABL-1:           ─────N₁₉─────TT
                TT─────

BCR-ABL-2            ─────N₁₉─────TT
                TT─────
```

Bcr-Abl-specific double stranded siRNAs were transfected into CD34+primary hematopoetic cells from CML patients. Cells, were purified to >95% and cultured as previously described (Scherr M. et al. Blood. 2002; 99: 709-712). Primary CD34+ are cultured in X-VIVO/1% HAS with recombinant human SCF (100 ng/ml), Flt-3-ligand (100 ng/ml each), and TPO (20 ng/ml) before electroporation, and GM-CSF and IL-3 (10 ng/ml each) is added thereafter.

The dsRNAs described above are transfected into these cells using the following protocol. DsRNAs are first added to $10^6$ cells in 100 μl RPMI1640 with 10% FCS to a final concentration of 200 nM and then electroporated in a 0.4 cm-wide electroporation cuvette at 300 V for 10 minutes using a Fischer Electroporator (Fischer, Heidelberg).

After a 15-minute incubation at room temperature, the cell suspension was transferred into fresh media (see above) and incubated a further 20 hours at 37° C., 5% $CO_2$, and 95% humidity prior to processing and analysis.

RNA Purification and Analysis

Cytoplasmic RNA was purified with the help of the RNeasy Kit (Qiagen, Hilden) and Bcr-abl mRNA levels were quantitated by real time RT-PCR.

Real Time PCR Analysis

Real-time Taqman-RT-PCR is performed as described previously (Eder M et al. Leukemia 1999; 13: 1383-1389; Scherr M et al. BioTechniques. 2001; 31: 520-526).

The probes and primers are:

```
bcrFP:            5'-AGCACGGACAGACTCATGGG-3',
                  (SEQ. ID NO: 15)

bcrFP:            5'-GCTGCCAGTCTCTGTCCTGC-3',
                  (SEQ. ID NO: 16)

bcr- Taqman-probe: 5'-AGGGCCAGGTCCAGCTGGACCC-3',
                  (SEQ. ID NO: 17) covering
                  the exon b5/b6 boundry, ablFP:            5'-GGCTGTCCTCGTCCTCCAG-3',
                  (SEQ. ID NO: 18)

ablRP:            5'-TCAGACCCTGAGGCTCAAAGT-3',
                  (SEQ. ID NO: 19)

abl-Taqman-probe: 5'-ATCTGGAAGAAGCCCTTCAGCGGC-
                  3',
                  (SEQ. ID NO: 20) covering
                  the exon 1a/6
```

Bcr-abl RNA levels in primary CD34+ hematopoietic cells from CML patients transfected with BCR-ABL siRNAs or control siRNAs (with or without hexaethylene glycol linker) are determined by real time RT-PCR and standardized against an internal control e.g. GAPDH mRNA levels.

---

We claim:

1. A method for inhibiting the expression of an AML-1/MTG-8 fusion gene in a mammalian cell in vitro, comprising the steps of:

a) introducing into a mammalian cell a dsRNA, said dsRNA comprising two separate non-linked RNA strands, a S1 strand and a complementary RNA strand, wherein said S1 strand consists of SEQ ID NO: 1 and said complementary strands consists of SEQ ID NO: 2, and b) maintaining the cell produced in step (a) under conditions and for a time sufficient to obtain degradation of mRNA of said target fusion gene, thereby inhibiting expression of said target fusion gene in the cell.

2. The method of claim 1, wherein each RNA strand is between 20 and 23 nucleotides in length.

3. The method of claim 1, wherein each RNA strand is 21 nucleotides in length.

4. The method of claim 1, wherein at least one of said RNA strands has a nucleotide overhang on the 3'-terminus.

5. The method of claim 1, wherein the cell is a leukocyte.

6. The method of claim 1, wherein the cell is a myelogenic cell.

7. The method of claim 1, wherein the RNA is produced by chemical synthesis.

8. The method of claim 1, wherein said S1 strand consists of SEQ ID NO: 1 and said complementary strand consists of SEQ ID NO: 2.

* * * * *